US007556623B2

(12) United States Patent
Lyman et al.

(10) Patent No.: US 7,556,623 B2
(45) Date of Patent: Jul. 7, 2009

(54) TOOL FOR USE WITH A MEDICATION VIAL AND/OR A SYRINGE

(75) Inventors: Scott D. Lyman, Tustin, CA (US); B. Cameron Smith, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 243 days.

(21) Appl. No.: 10/910,064

(22) Filed: Aug. 3, 2004

(65) Prior Publication Data

US 2005/0056121 A1 Mar. 17, 2005

Related U.S. Application Data

(60) Provisional application No. 60/499,829, filed on Sep. 3, 2003.

(51) Int. Cl.
*A61M 5/32* (2006.01)

(52) U.S. Cl. .................................. 604/414; 206/365

(58) Field of Classification Search ............... 81/3.2, 81/3.07; 604/181, 86, 110, 192, 263, 414; 141/2; 206/365, 366

See application file for complete search history.

(56) References Cited

U.S. PATENT DOCUMENTS

| 1,090,422 | A | 3/1914 | Stovall et al. |
|---|---|---|---|
| 1,511,522 | A | 10/1924 | Rolsky |
| 2,077,240 | A | 4/1937 | Jeffords |
| 2,728,250 | A | 12/1955 | Robert |
| 3,469,750 | A | 9/1969 | Vanderbeck |
| 4,178,646 | A | 12/1979 | Swartz et al. |
| 4,375,849 | A | 3/1983 | Hanifl |
| 4,466,538 | A | 8/1984 | Gianni |
| 4,494,652 | A | 1/1985 | Nelson et al. |
| 4,596,562 | A | 6/1986 | Vernon |
| 4,615,242 | A | 10/1986 | Milin |
| 4,658,957 | A | 4/1987 | Guth et al. |
| 4,717,386 | A | 1/1988 | Simmons |
| 4,726,264 | A | 2/1988 | Bost |
| 4,742,910 | A | 5/1988 | Staebler |
| 4,836,373 | A | 6/1989 | Goldman |
| 4,844,249 | A | 7/1989 | Coulombe |

(Continued)

FOREIGN PATENT DOCUMENTS

JP 2000-316919 11/2000

*Primary Examiner*—Nicholas D Lucchesi
*Assistant Examiner*—Christopher D Koharski
(74) *Attorney, Agent, or Firm*—Marshall, Gerstein & Borun LLP

(57) ABSTRACT

A tool for use with a medication vial and a syringe includes a housing having a top side, a bottom side, and a surrounding edge. A slotted aperture is defined in the housing and including a flange shaped to engage a vial cap. A cylindrical aperture is defined in the housing and sized to permit placement of a forward portion of the syringe including a cap into the cylindrical aperture. An actuator button is mounted to the housing, and a gripper is mounted within the housing having a pair of opposed edges. The gripper is responsive to movement of the actuator button to permit movement of the edges between a retracted position in which the edges are disposed away from a central portion of the cylindrical aperture, and an extended position in which the edges are displaced toward the central portion of the cylindrical aperture.

46 Claims, 12 Drawing Sheets

U.S. PATENT DOCUMENTS

| | | |
|---|---|---|
| 4,846,803 A | 7/1989 | Emerson |
| 4,852,844 A | 8/1989 | Villaveces |
| 4,863,451 A | 9/1989 | Marder |
| 4,869,133 A | 9/1989 | Irazoqui et al. |
| 4,915,225 A | 4/1990 | Tabor, Jr. et al. |
| 4,915,698 A | 4/1990 | Levenson |
| 4,921,199 A | 5/1990 | Villaveces |
| 4,955,865 A | 9/1990 | Steiner et al. |
| 4,979,945 A | 12/1990 | Wade et al. |
| 4,986,816 A * | 1/1991 | Steiner et al. ............... 604/192 |
| 4,989,307 A | 2/1991 | Sharpe et al. |
| 5,007,535 A | 4/1991 | Meseke et al. |
| 5,024,666 A | 6/1991 | Pituch |
| 5,035,703 A | 7/1991 | Baskas |
| 5,037,400 A | 8/1991 | Curry |
| 5,067,223 A | 11/1991 | Bruno |
| 5,067,948 A | 11/1991 | Haber et al. |
| 5,102,083 A | 4/1992 | Baskas |
| 5,160,324 A | 11/1992 | Halbach |
| 5,242,426 A | 9/1993 | Pituch |
| 5,279,577 A | 1/1994 | Collett |
| 5,343,875 A | 9/1994 | Chase |
| 5,346,086 A | 9/1994 | Harris |
| 5,348,543 A | 9/1994 | Talley |
| 5,356,384 A | 10/1994 | Haber |
| 5,356,385 A * | 10/1994 | Latini ........................ 604/110 |
| 5,469,964 A | 11/1995 | Bailey |
| 5,495,941 A | 3/1996 | Leonard |
| 5,564,565 A | 10/1996 | Yamada |
| 5,588,966 A * | 12/1996 | Atsumi ...................... 604/110 |
| 5,607,403 A | 3/1997 | Kretzschmar et al. |
| 5,624,412 A | 4/1997 | Weekley |
| 5,791,471 A | 8/1998 | Radmand |
| 5,975,295 A | 11/1999 | Diamond |
| 6,036,671 A | 3/2000 | Frey |
| 6,247,592 B1 | 6/2001 | Racicot et al. |
| 6,257,408 B1 | 7/2001 | Odierno |
| 6,279,743 B1 | 8/2001 | Ballard et al. |
| 6,581,648 B1 * | 6/2003 | Zolentroff et al. .............. 141/2 |
| 6,591,984 B2 | 7/2003 | Odierno et al. |
| 6,604,903 B2 | 8/2003 | Osborne et al. |
| 2001/0035362 A1 | 11/2001 | Odierno et al. |
| 2002/0195362 A1 | 12/2002 | Abe |
| 2003/0116569 A1 | 6/2003 | Mercier |

* cited by examiner

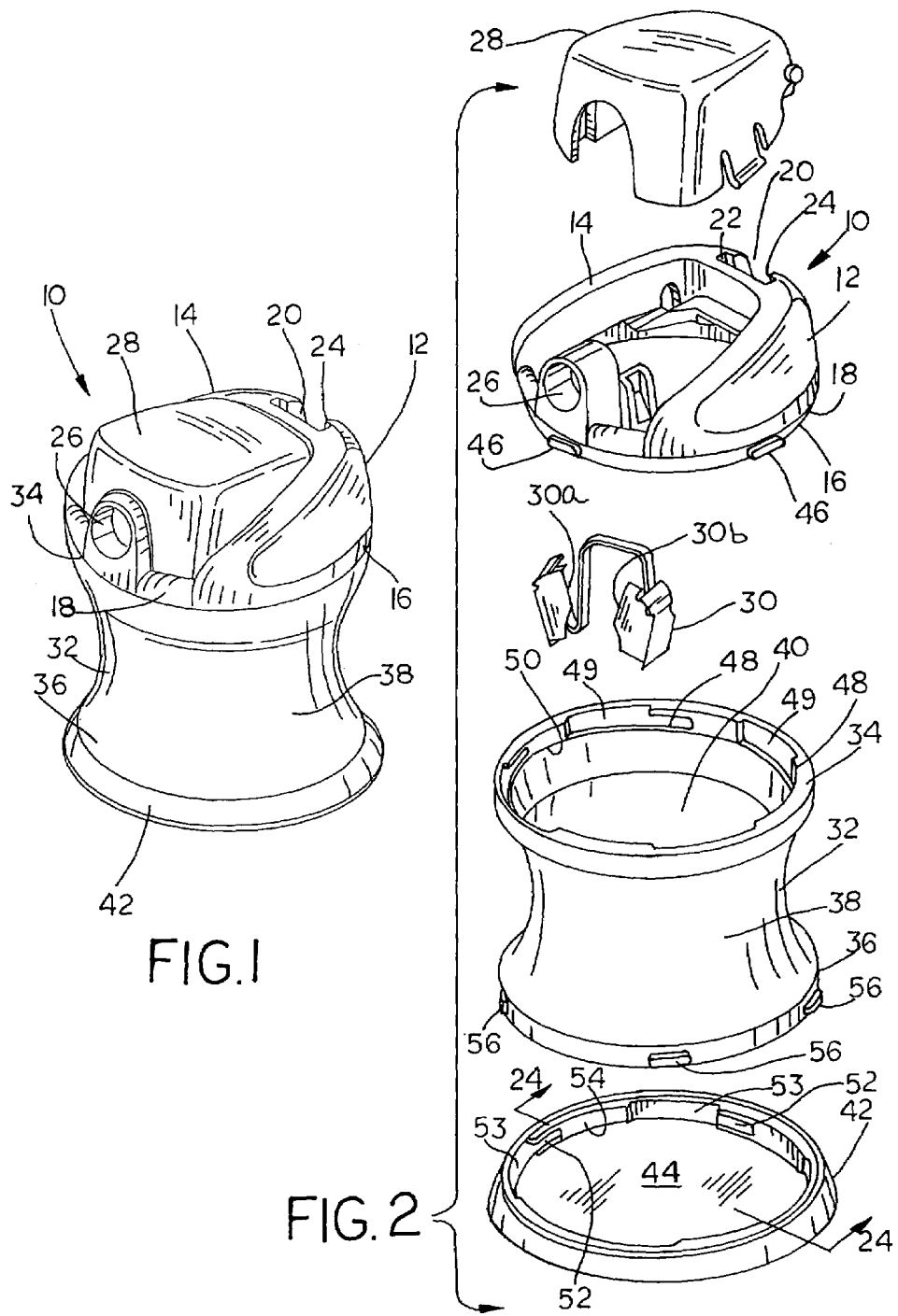

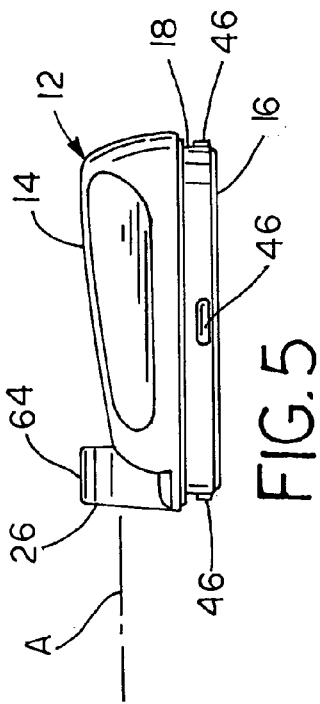
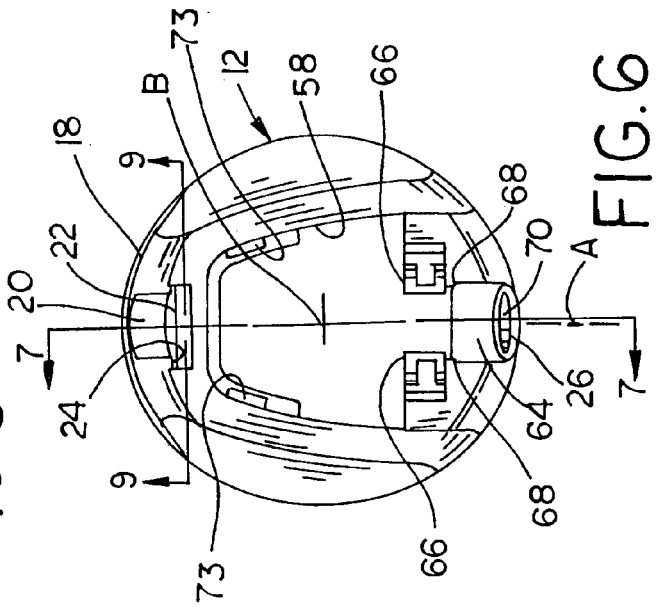
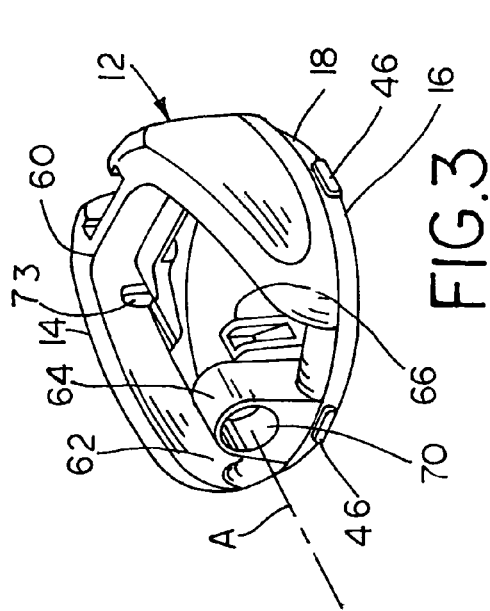
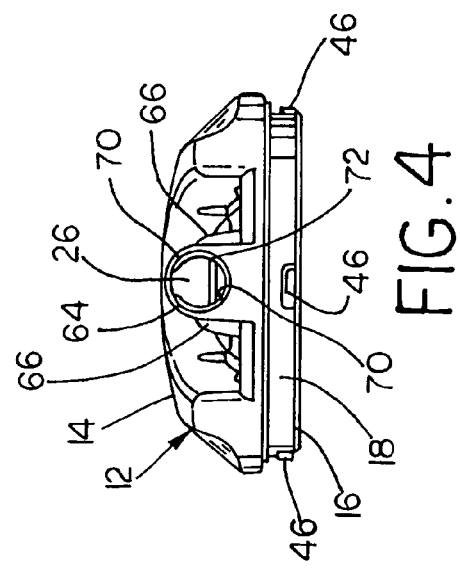

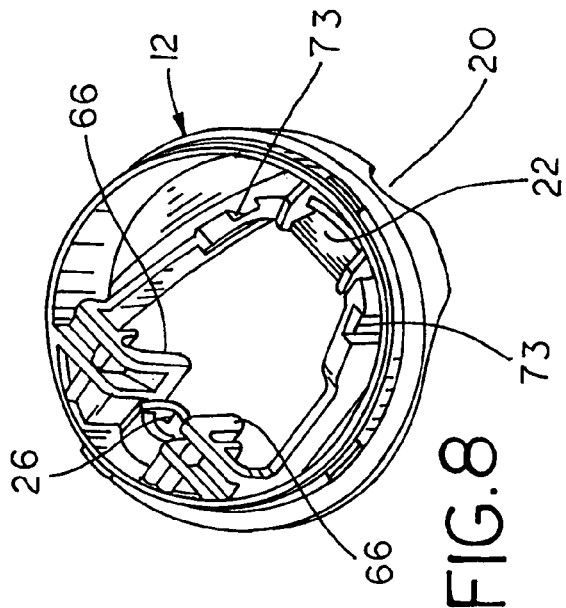
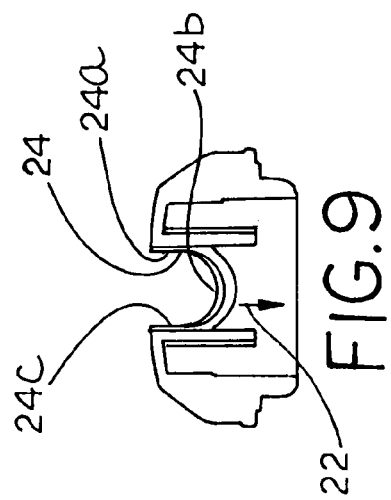
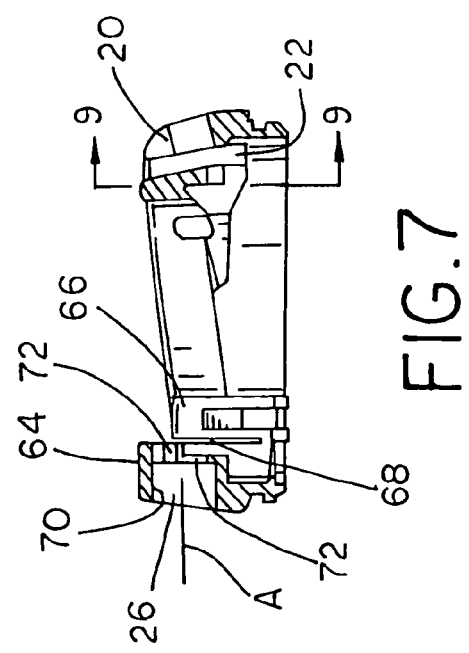

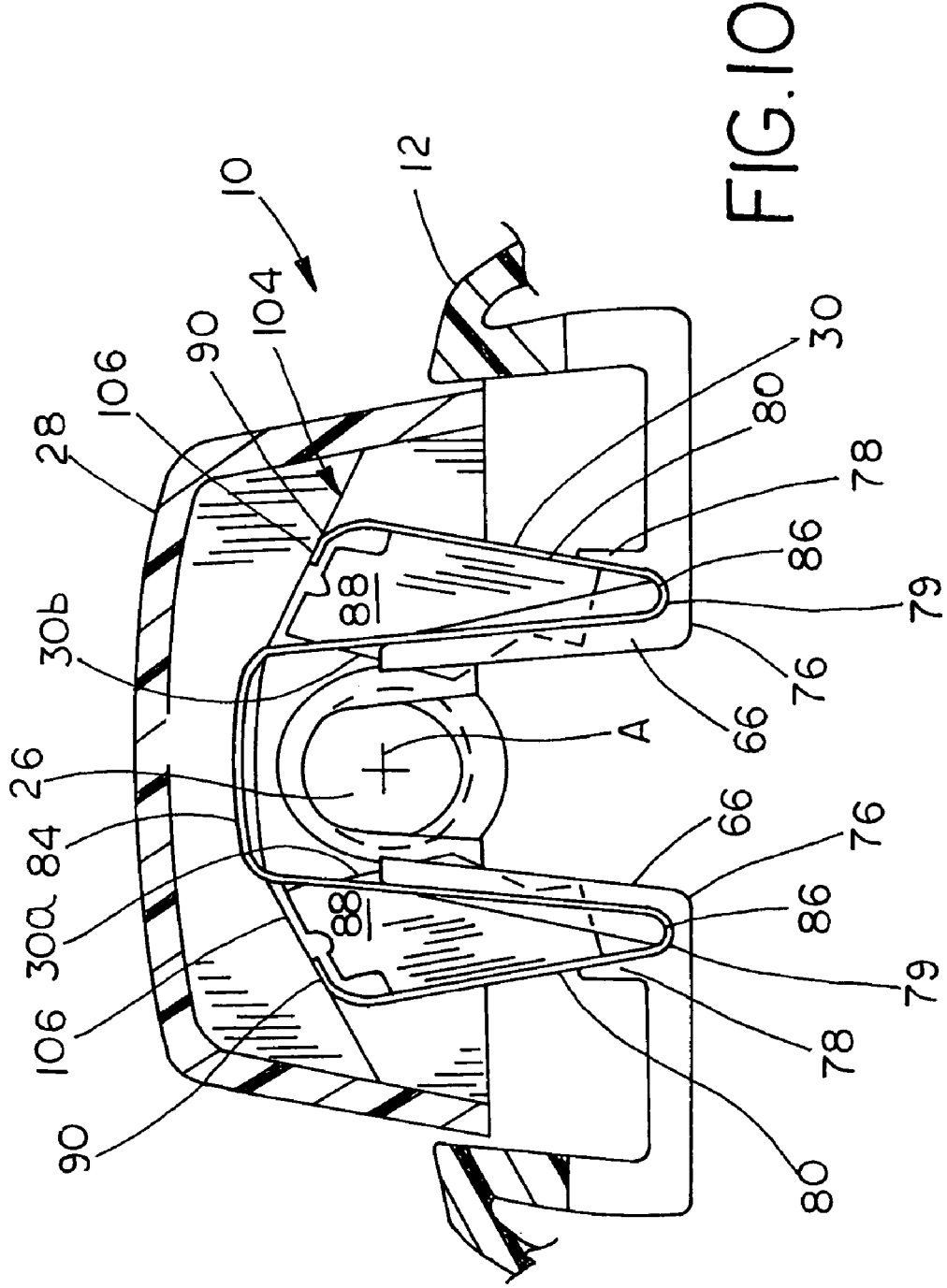

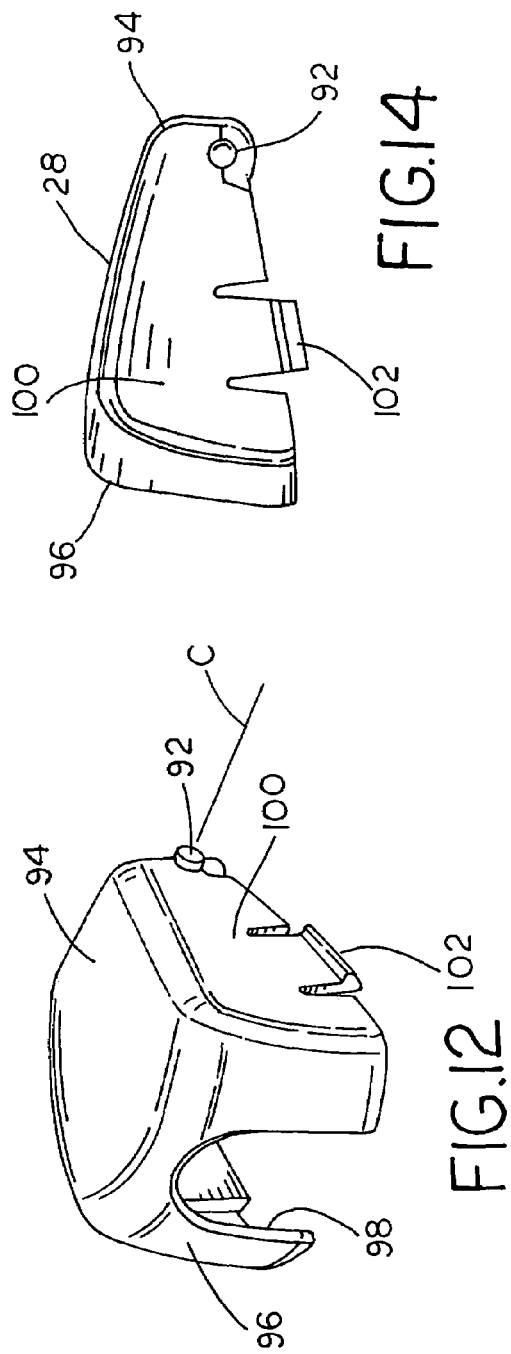

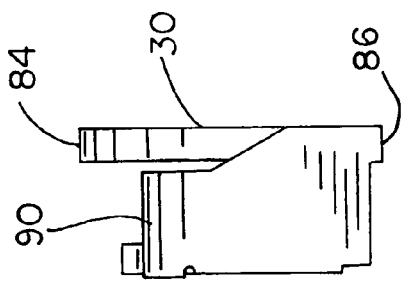
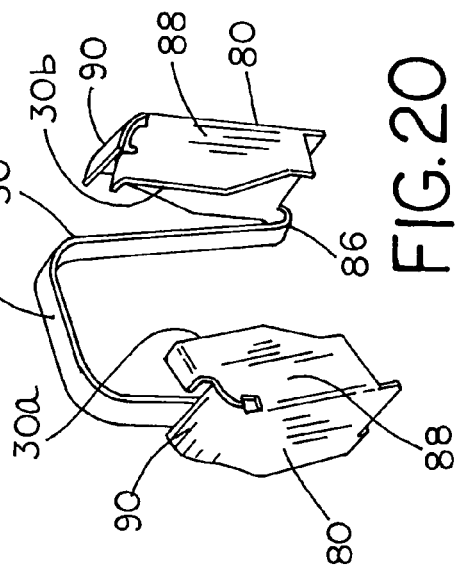
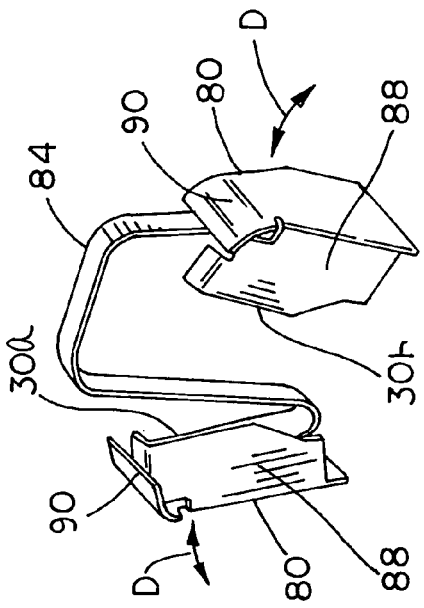
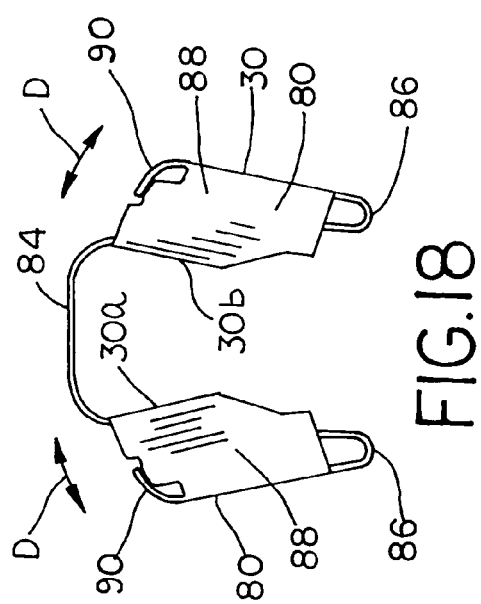

TOOL FOR USE WITH A MEDICATION VIAL AND/OR A SYRINGE

CROSS REFERENCE TO RELATED APPLICATION

This application is a non-provisional application claiming priority from U.S. Provisional Application Ser. No. 60/499,829, filed Sep. 3, 2003, entitled "Tool for Use with a Medication Vial and/or a Syringe" and incorporated herein by reference in its entirety.

FIELD OF THE INVENTION

The present invention relates generally to a tool for use with a vial of medication and/or a syringe for delivering medication and, more specifically, to a tool that permits easy removal of the cap from a vial of medication and that also permits the removal of certain protective components commonly found on a syringe.

BACKGROUND OF THE INVENTION

Many forms of medication require the patient to prepare and inject the required dosage using a syringe. In certain circumstances, the patient or other user may be required to undertake a number of preparatory steps in order to get the dosage ready for injection. However, some patients may be prone to infection and/or other complications. Therefore, a number of cautionary steps are typically advisable when preparing the medication for injection in order to reduce the chances of such complications.

Many medications are often prepared and injected by the user. Such medications typically are packaged and sold in a small vial having a removable lid or cap which covers a rubber stopper. Care must be taken when removing the cap so as not to contaminate either the rubber stopper or the medication contained in the small vial. After the cap is removed, the vial remains covered by the rubber stopper. As would be known, a needle or an adapter may be used to penetrate the rubber stopper, thus providing access to the medication contained within the vial. For some powdered medications, first a diluent must be injected into the vial using the adapter, thus permitting the user to mix and then extract the medication using the syringe/needle.

The syringe used to inject the dose of medication into the user is typically shipped or stored without having the needle in place. Instead, the forward end of the syringe is typically covered by a protective tip cap. When the user is preparing to inject the medication, this tip cap must be removed and replaced with the needle. The needle itself is provided with a protective cover, which permits the user to attach the needle to the forward end of this arranged without contaminating the needle itself. This protective cover must be removed prior to injection. Again, care must be taken to avoid contaminating the needle.

At least some patients may experience some degree of difficulty removing the vial cap, removing the tip cap, and/or removing the needle cover. Therefore, it may be desirable to provide a tool which assists the user in easily and effectively removing the aforementioned components.

BRIEF DESCRIPTION OF THE DRAWINGS

FIG. 1 is a perspective view of a tool assembled in accordance with the teachings of the present invention;

FIG. 2 is an exploded view in perspective of the tool illustrated in FIG. 1;

FIG. 3 is a perspective view of the housing;

FIG. 4 is a front elevational view thereof;

FIG. 5 is a side elevational view thereof;

FIG. 6 is a top plan view thereof;

FIG. 7 is a cross-sectional view taken along line 7-7 of FIG. 6;

FIG. 8 is a perspective view of the housing taken from below;

FIG. 9 is a fragmentary cross-sectional view taken along line 9-9 of FIG. 6;

FIG. 10 is an enlarged fragmentary cross-sectional view illustrating the camming surface on the actuating button in contact with an upper part of the gripper;

FIG. 12 is an enlarged perspective view of the actuator button;

FIG. 13 is an enlarged front elevational view of the actuator button;

FIG. 14 is an enlarged side elevational view of the actuator button;

FIG. 17 is a perspective view of the gripper;

FIG. 18 is a front elevational view thereof;

FIG. 19 is a side elevational view thereof;

FIG. 20 is a perspective view of the gripper taken from below;

DETAILED DESCRIPTION OF THE PREFERRED EMBODIMENT

Figure 11:
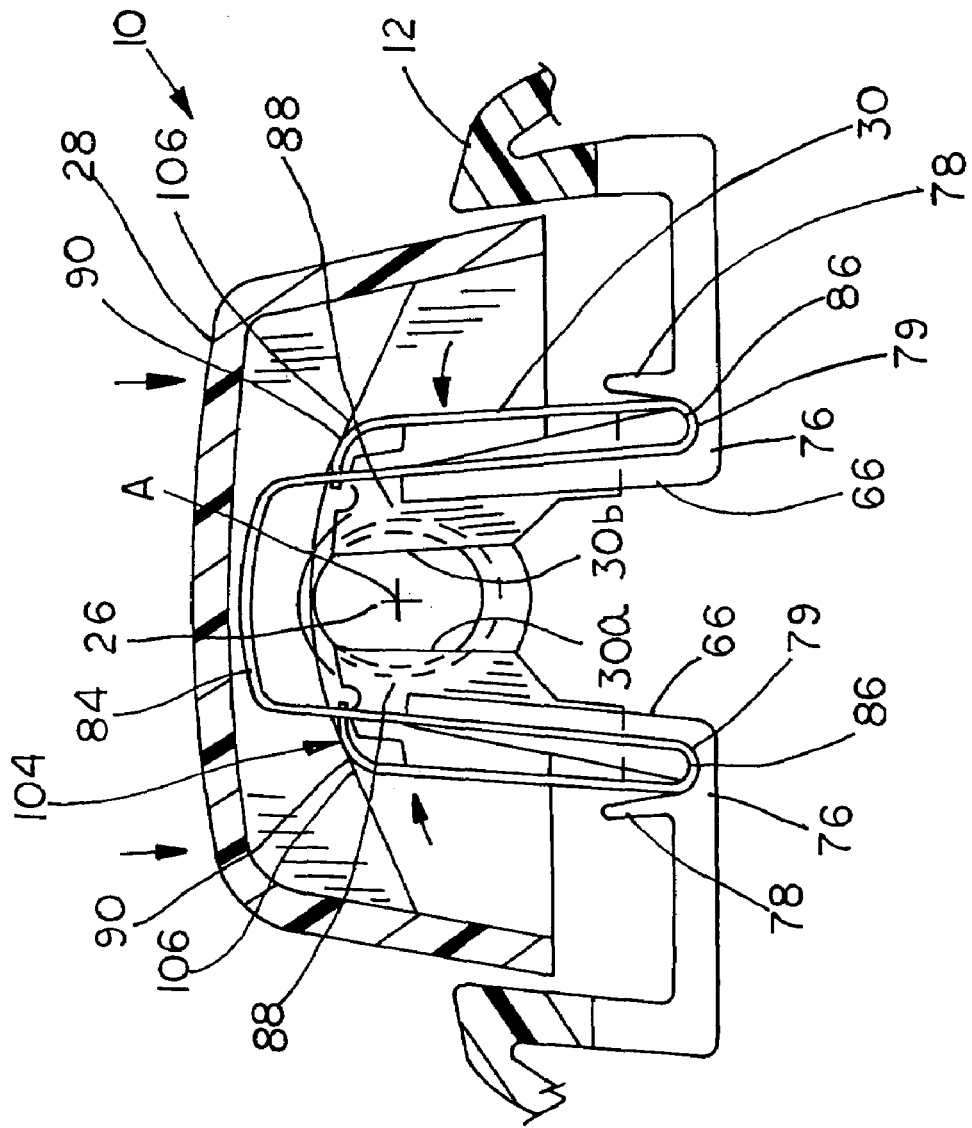
FIG. 11 is an enlarged fragmentary cross-sectional view similar to FIG. 10 but showing the actuating button depressed and shifting the edges of the gripper toward the center of the aperture.

The example described herein is not intended to be exhaustive or to limit the scope of the invention to the precise form or forms disclosed. Rather, the following exemplary embodiment has been chosen and described in order to best explain the principles of the invention and to enable others skilled in the art to follow the teachings thereof.

Referring now to FIGS. 1 and 2 of the drawings, a tool assembled in accordance with the teachings of the present invention is shown and is generally referred to by the reference 10. The tool 10 includes a housing 12 having a top side 14, a bottom side 16, and a peripheral or surrounding edge 18. The housing 12 also includes a first aperture 20. A slot 22 along with a flange 24 are defined in the housing 12 adjacent the first aperture 20 (both the slot 22 and the flange 24 are best viewed in FIGS. 3, 6, 7 and 9). The housing 12 further includes a second aperture 26 which, in the disclosed example, is disposed on a side of the housing 12 opposite to the aperture 20. An actuator button 28 is mounted to the housing 12 and is movable between a first position and a second position as will be discussed in greater detail below. A gripper 30 is mounted to the housing 12 generally adjacent to the second aperture 26 (the gripper 30 is concealed in FIG. 1, and is best viewable in FIGS. 2, 10-11 and 17-20).

As shown in FIGS. 2, 10 and 17-20, the gripper 30 includes a pair of edges 30a and 30b. The gripper 30 is mounted within the housing 12 such that the edges 30a and 30b are responsive to shiftable movement of the actuator button 28 as will be explained in greater detail below.

Referring again to FIGS. 1 and 2, the tool 10 may include an optional reservoir 32. The reservoir includes an upper edge 34, a lower edge 36, and a central portion 38 defining an internal cavity 40 (the internal cavity visible in FIG. 2). In the disclosed example, the reservoir 32 is open on both the upper edge 34 and the lower edge 36. The tool 10 may also include an optional base 42, with the base 42 preferably having a closed bottom 44 visible in FIG. 2. As will be explained in greater detail below, the housing 12 may be attached to the upper edge 34 of the reservoir 32, while the lower edge 36 of the reservoir 32 may be attached to the base 42. Alternatively, the housing 12 may be attached directly to the base 42.

As shown in FIG. 2, the surrounding edge 18 of the housing 12 includes a plurality of protruding tabs 46 disposed generally adjacent the bottom side 16. The tabs 46 of the housing 12 are sized for insertion in any one of a plurality of corresponding slots or depressed grooves 48 in the reservoir 32. As shown in FIGS. 2 and 21-23, the grooves 48 are defined on an inner edge 50 of the reservoir 32 generally adjacent to the upper edge 34. Each of the grooves 48 includes an upwardly facing opening 49 (FIGS. 2 and 22), with the openings 49 sized to permit an appropriate one of the corresponding tabs 46 to be placed into the groove 48 from above. The housing 12 can then be attached to the reservoir 32 by placing the tabs 46 in the corresponding openings 49 and twisting the housing 12 relative to the reservoir 32 such that the tabs 46 engage and are retained in the grooves 48.

Figure 25:
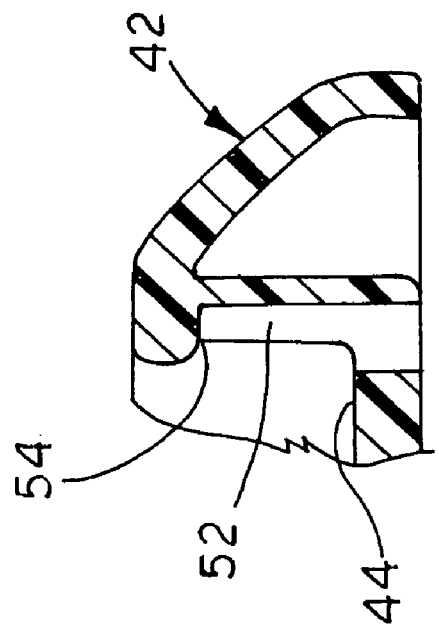
FIG. 25 is an enlarged fragmentary cross-sectional view taken about the circumscribed portion of FIG. 24.
Figure 24:
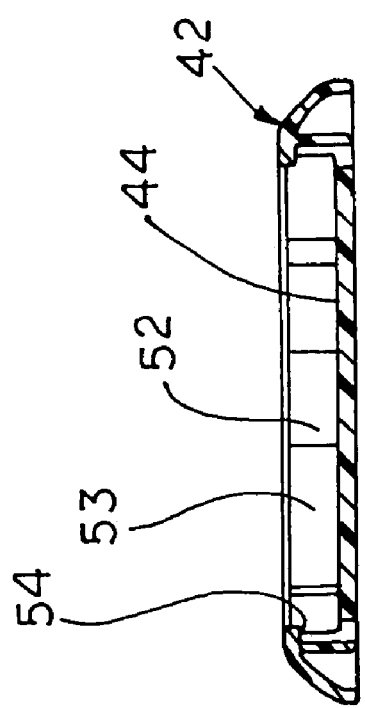
FIG. 24 is a cross-sectional view taken along line 24-24 of FIG. 2.

Similarly, and referring now to FIGS. 2 and 24-25, a plurality of slots or grooves 52 are defined on an inner edge 54 of the base 44. The lower edge 36 of the reservoir 32 includes a plurality of protruding tabs 56 (shown in FIGS. 2 and 21-22), which are sized to engage any one of the plurality of grooves 52 defined on the base 44. Each of the grooves 52 includes an upwardly facing opening 53 (FIGS. 2 and 24), with the openings 53 sized to permit the tabs 56 to be placed into the groove 52 from above. The reservoir 32 can then be attached to the base 44 by placing each of the tabs 56 in a corresponding one of the openings 53 and twisting the reservoir 32 relative to the base 44 such that the tabs 56 engage and are retained in the grooves 52. Optionally, the housing 12 may be attached directly to the base 44 by inserting the tabs 46 into the openings 53 in the base 44, and twisting the housing 12 relative to the base 44 such that the tabs 56 are frictionally retained in the appropriate grooves 52.

Referring now to FIGS. 3-8, the housing 12 includes a cutout 58 sized to receive the shiftable actuator button 28. The cutout 58 includes a first end 60 and a second end 62, with the first end 60 being disposed generally adjacent to the first aperture 20, and the second aperture 26 being generally disposed adjacent the second end 62. In the disclosed example, the second aperture 26 is formed in an upright 64 which extends upwardly from adjacent the peripheral edge 18 of the housing 12. A pair of uprights 66 are formed in the housing generally adjacent to the upright 64, with each of the uprights 66 separated from the upright 64 by a slot 68, with the slots 68 sized to receive a portion of the gripper 30 as will be explained in greater detail below. The aperture 26 includes a longitudinal axis A, which in the disclosed example extends generally toward a center B (FIG. 6) of the generally round housing 12 and further extends generally horizontal when the tool 10 is disposed in the upright and preferred use position of FIG. 1. The housing 12 is generally round in the disclosed example, but other shapes will likely prove suitable as well.

As shown in FIGS. 3 and 4, the aperture 26 includes a generally cylindrical inner surface 70 which is sized to receive a forward portion of a syringe as will be discussed in greater detail below. Also, as is shown in FIGS. 4 and 7, the aperture 26 includes an inner end defined by a flange 72 which, in the disclosed example, forms a stop to limit the travel of the forward portion of the syringe into the aperture 26 as will be explained below. As shown in FIGS. 3, 6 and 8, the housing 12 preferably includes a pair of pivot apertures 73 which are sized and disposed to pivotally receive a portion of the actuator button 28.

As shown in FIG. 9, the flange 24 of the first aperture 20 includes a pair of side portions 24a and a lower portion 24b. In the disclosed example, the side portions 24a are generally straight, while the lower portion 24b is generally curved and is shaped to correspond roughly to the curvature of a curved neck of the medication vial (shown in FIGS. 26-28). Also, as will be explained below, in the preferred form of usage the slot 22 is defined through the housing 12 and permits a cap 128 of a medication vial 126 to pass through the housing 12 and into the reservoir 32 (should the tool 12 be provided with the optional reservoir 32) when the cap 128 is removed from the medication vial 126.

Referring now to FIGS. 10 and 11, the gripper 30 is shown disposed within the housing 12 beneath the actuator button 28. Each of the uprights 66 includes a base 76, with a protrusion, tab or flange 78 defined in the housing 12 generally adjacent to the base 76 of each upright 66, thereby forming a seat 79 sized to receive a lower part of the gripper 30.

The gripper 30 includes a pair of pivoting arms 80, each of which defines a corresponding one of the edges 30a, 30b. Each of the arms 80 is attached to a central portion 84, with each of the arms 80 pivoting about a corresponding bend, elbow or pivot 86. It will be understood that, in the disclosed example, the gripper 30 is formed of spring steel, or any other suitable material, such that the arms 80 will be generally spring biased relative to the central portion 84. In the disclosed example, the edges 30a, 30b of the arms 80 are formed by a relatively thin plate or panel 88, with the panels 88 sized to be disposed in the slot 68 (shown in FIGS. 3 and 6), such that the arms 80 and hence the edges 30, 30b will be able to shift or pivot freely about their respective pivots 86, such that the edges 30a and 30b of the arms 80 are moved toward and away from the axis A of the aperture 26 (depending on whether the actuator button 28 is depressed or released, respectively) with the panels 88 sliding through or otherwise guided by the slots 68. Preferably, each of the arms 80 is provided with a camming surface 90 which, in the disclosed example, is generally curved.

Referring now to the FIGS. 12-16, the actuator button 28 is shown. The actuator button 28 includes a pair of pivots 92 disposed adjacent a rear end 94, with the pivots 92 sized to be received in the apertures 73 of the housing 12. Thus, the actuator button 28 will pivot relative to the housing 12 about a generally horizontal axis C (FIGS. 12 and 16) which, in the disclosed example, extends through the pivots 92. A forward end 96 of the actuator button 28 includes a cutout 98. The cutout 98 is sized to fit over the upright 64 formed in the housing 12 (the upright 64 being visible in FIGS. 3-7), such that the actuator button 28 will pivot freely relative to the housing 12 about the horizontal axis C without interference from the upright 64. The pivots 92 are preferably sized such that the actuator button may be snapped in place onto the housing 12 with the pivots 92 disposed within the apertures 73. The actuator button 28 includes a pair of sides 100, with each of the sides preferably provided with a retaining tab 102. The retaining tabs 102 are preferably sized to engage an inner surface of the aperture 58 formed in the housing 12 in order to limit the upward rotation or movement of the actuator button 28.

Figure 16:
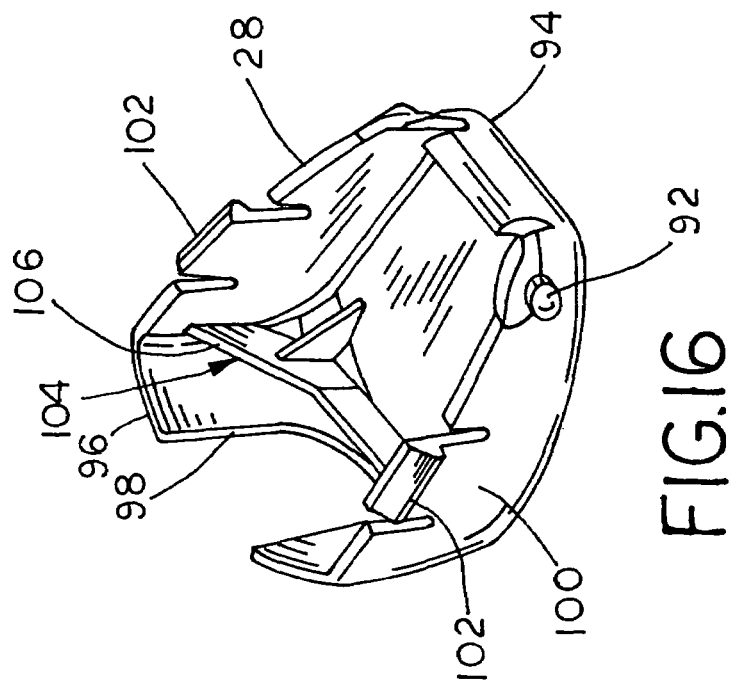
FIG. 16 is a perspective view of the actuator button taken from below.
Figure 15:
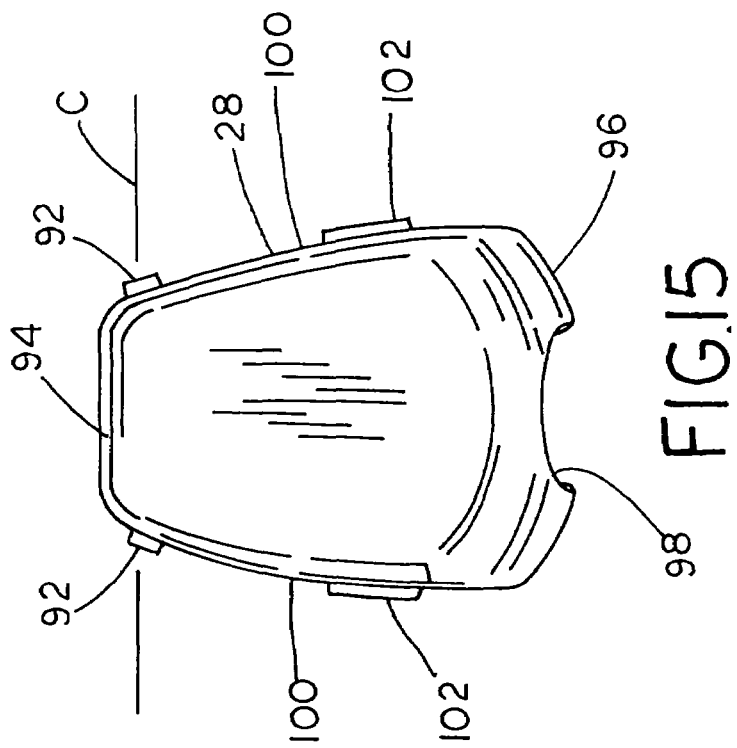
FIG. 15 is an enlarged top plan view of the actuator button.
Figure 23:
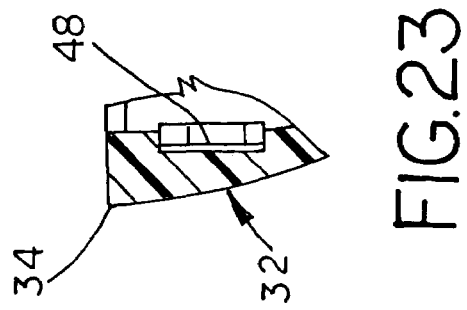
FIG. 23 is an enlarged fragmentary cross-sectional view taken about the circumscribed portion of FIG. 22.
Figure 22:
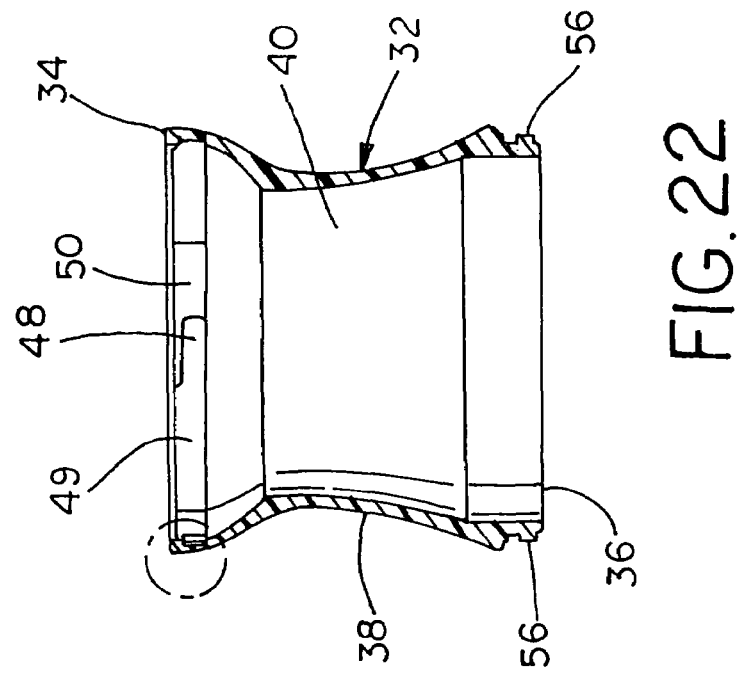
FIG. 22 is a cross-sectional view taken along line 22-22 of FIG. 21.
Figure 21:
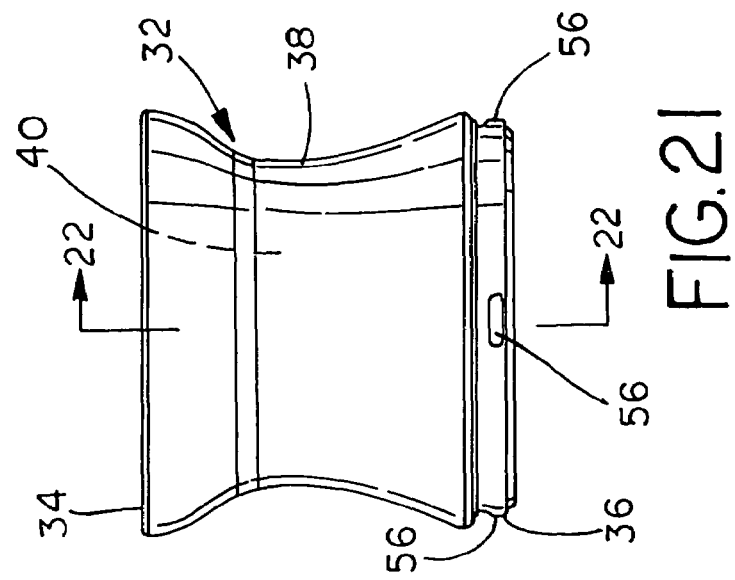
FIG. 21 is an elevational view of the reservoir.

As shown in FIGS. 13 and 16, a camming surface 104 is defined on an underside of the actuator button 28. The camming surface 104 includes a pair of angled sections 106, which are disposed to make contact with the corresponding camming surface 90 on the arms 80 of the gripper 30 (the camming surfaces 90 being visible in FIGS. 17-20). Consequently, the angled surfaces 106 will, in the disclosed example, cooperate with the camming surfaces 90 in response to the pressing of the actuator button 28, thus causing the arms 80 of the gripper 30 to pivot about their respective pivot points 86, enabling the arms 80 to travel along a generally arcuate and generally inward path indicated by the reference arrows D in FIGS. 17 and 18. Thus, by depressing the button 28 it will be appreciated that the edges 30a and 30b of the gripper 30 will be shiftable toward the axis A of the aperture 26.

Figure 26:
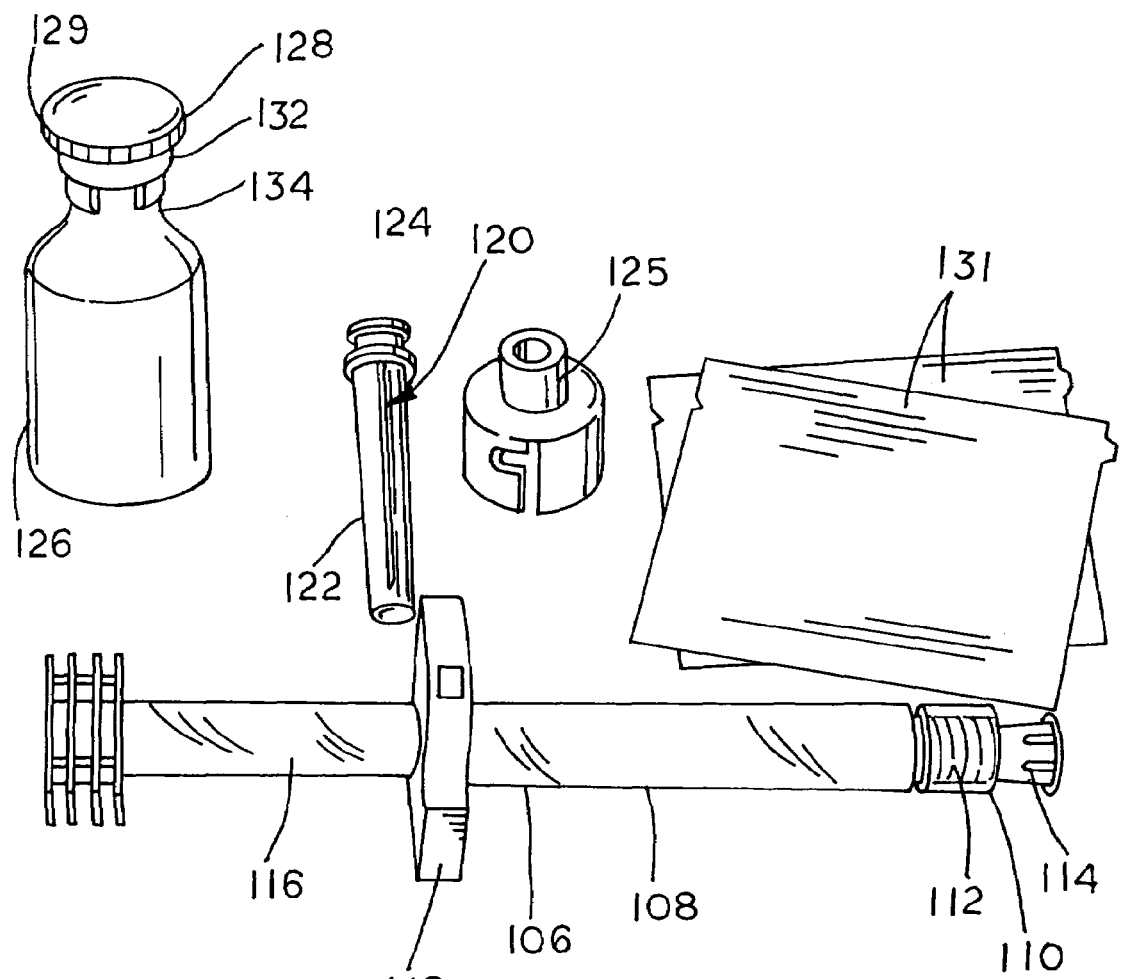
FIG. 26 illustrates a medication vial having a removable cap, a syringe shown with a tip cap in place, a separate hypodermic needle shown with a needle cover in place, and an adapter that attaches to the syringe.

Referring now to FIG. 26, a syringe 106 of the type commonly employed when injecting a dosage of medication is shown. The syringe 106 includes a generally cylindrical forward end 108 terminating in a tip 110. Typically, the tip 110 includes threads 112, and is preferably covered by a tip cap 114. In the disclosed example, the threads 112 are formed in a LUERLOK® hub which is commonly found on syringes. It will be appreciated that the threads 112 are internally formed in a cylindrical forward barrel or end 113. The syringe 106 also includes a plunger 116, and a suitable handle 118. It will be understood that the tip cap 114 is removable as will be explained below. A hypodermic needle 120 of the type commonly employed in the art in conjunction with the syringe 106 includes a needle cover 122 covering the needle 120 (the needle 120 is shown in FIG. 26 and in partial cutaway in FIG. 30). The syringe 106 also includes an end 124 sized and adapted to be attached to the forward end 110 of the syringe 106 using the threads 112. It will be understood when viewing either FIG. 26 (or FIG. 30) that the needle cover 122 is removable to expose the hypodermic needle 120. An adapter 125 may be provided, with the adapter 125 also being provided with suitable threads sized to enable the adapter 125 to be attached to the threads 112 of the syringe 106. The adapter 125 is typically provided with a sharp protrusion (not shown) as would be known, and enables the adapter 125, when suitably attached to the syringe 106, to penetrate a seal on the medication vial 126, in order to permit flow communication between the syringe 106 and the interior of the medication vial 126. Alcohol swabs 131 may prove useful and may generally be advised.

Figure 27:
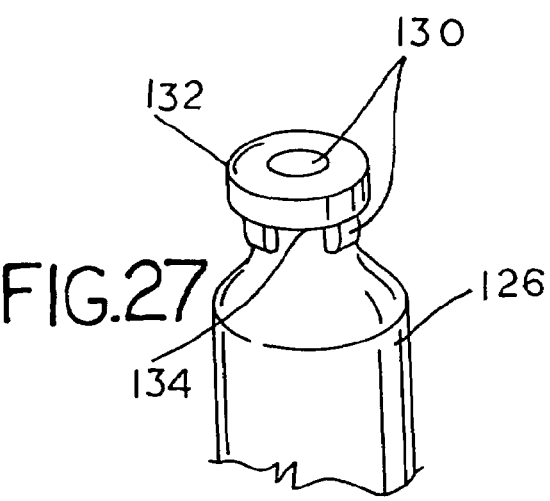
FIG. 27 is an enlarged fragmentary view in perspective of a medication vial shown with the removable cap removed.
Figure 29:
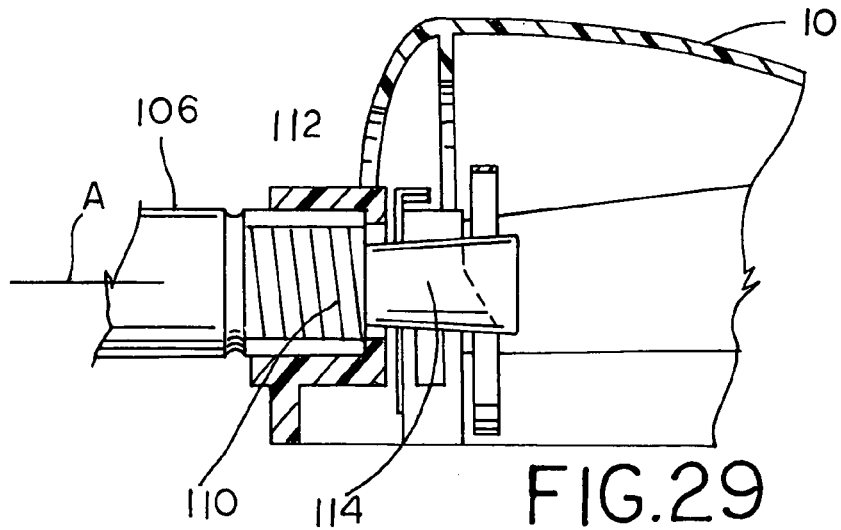
FIG. 29 is an enlarged fragmentary cross-sectional view illustrating the syringe in position in the tool in preparation for removing the tip cap from the syringe.

The medication vial 126 includes a removable plastic lid or cap 128 of the type commonly employed in the art. The cap 128 covers a rubber stopper 130, and a metal retaining ring 132 serves to retain the rubber stopper 130 in place as would be known. The rubber stopper 130 is substantially concealed by the cap 128 in FIG. 26, but is visible with the cap removed as is shown in FIG. 27. The medication vial 126 as shown includes a rounded neck 134. It will be understood that the metal ring 132 and the rubber stopper 130 are typically covered by the cap 128, and it will further be appreciated that the cap 128 is removable by grasping an appropriate edge portion 129 (FIGS. 26 and 28) of the cap 128. It will be noted that, in some applications, the rubber stopper may be covered with a polymer coating as would be known.

In operation, the tool 10 may be used with or without the optional reservoir 32 and/or the optional base 44. When it is desired for a user (not shown) to use the tool 10 to prepare and/or inject an appropriate dose of medication contained within the medication vial 126, the user may follow the following exemplary steps. It will be understood that, throughout the steps outlined here in, the user will follow appropriate procedures, such as the liberal use of alcohol swabs, in accordance with generally accepted practices which are made available to the user by the medical community and/or the manufacturer of the medication and/or the manufacturer of the syringe.

Figure 28:
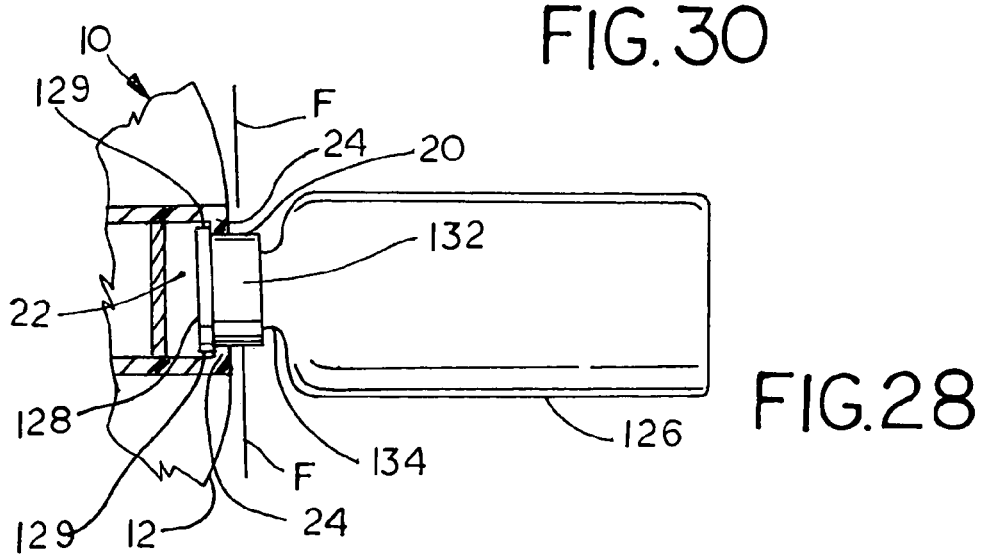
FIG. 28 is an enlarged fragmentary plan view illustrating the medication vial disposed in one of the apertures in a position for removing the cap.

First, the user will find it necessary to remove the cap 128 from the medication via 126. This may be accomplished by positioning the medication vial 126 in the aperture 20 of the housing 12 as shown in FIG. 28. With the medication vial 126 so positioned, the user can manipulate the medication vial 126 by pushing the bottom of the vial 126 downward, as shown by the reference arrow E, which in FIG. 28 extends into the plane of the Figure, such that the cap 128 engages the flange 24 defined adjacent the aperture 20 of the housing 12. By rotating the medication vial 126 generally about an appropriate axis F as shown, the cap 128 will be released from the medication vial 126 in a fashion similar to removing a lid from a pop bottle. Should the tool be used in conjunction with the reservoir 32, it will be appreciated that the cap 128 will fall through the slot disposed adjacent the aperture 20 and into the reservoir 32.

Another preparatory step is the removal of the tip cap 114 from the syringe 106. In order to accomplish this, and with the tool 10 positioned substantially as shown in FIG. 1, the forward portion 110 of the syringe 106 is inserted into the aperture 26, with a longitudinal axis of the syringe 106 oriented substantially parallel to the axis A of the cylindrical aperture 26. Preferably, there is a suitably tight fit between the cylindrical end 113 of the forward portion 110 of the syringe 106 and the interior of the aperture 26, such that the syringe 106 will be suitably maintained generally parallel to the axis A without excessive play.

With the syringe 106 in this position, the actuator button 28 is depressed by the user such that the button 28 rotates about the axis C. By cooperation of the angled surfaces 106 on the actuator button 28 and the camming surfaces 90 carried by the arms 80 of the gripper 30, the edges 30a, 30b on the arms 80 will shift between the retracted position shown in FIG. 10 and the extended position shown in the FIG. 11. Upon the shifting movement of the edges 30a and 30b toward the centerline or axis A of the aperture 26, the edges 30a and 30b may be brought into engagement with the tip cap 114. By maintaining at least a slight downward force on the actuator button 28, the tip cap 114 is then easily removable or separated from the syringe 106 by withdrawing the syringe 106 from the aperture 26 of the housing 12.

At this point, the adapter 125 may be attached to the threaded portion 112 of the syringe 106 in a known manner. The user may then position an upper end of the medication vial 126 into a cylindrical receiving area 127 of the adapter 125. Once this is accomplished, the sharp protrusion (not shown) pierces the rubber stopper 130 of the medication vial 126 as would be known. At this point, diluent disposed within the syringe 106 may be injected into the medication vial 126 (which, in the disclosed example, contains medication in a powdered form). Upon injection of the diluent, the user then suitably mixes the powdered medication with the diluent within the medication vial 126 in accordance with instructions made available by the medical community.

Figure 30:
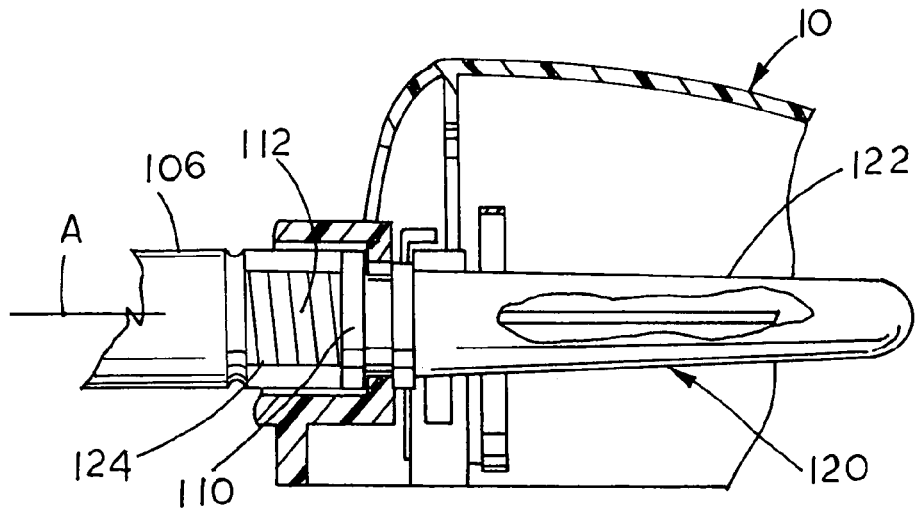
FIG. 30 is an enlarged fragmentary cross-sectional view illustrating the syringe in position in the tool in preparation for removing the needle cover from the syringe.

After the medication is suitably mixed and ready for injection, the medication vial 126 and the still attached adapter 125 may be detached from the syringe 106. At this point, the user must attach the needle 120 to the syringe 106 by securing the end 124 of the needle 122 the threads 112 adjacent the forward portion 110. When the needle 120 is properly attached, the needle cover 122 must be removed. Once again the syringe 106 is inserted into the aperture 26 of the housing 12 as shown in FIG. 30. Again, when the forward end of the threaded portion 112 makes suitable contact with the stop defined by the flange 72 within the cylindrical aperture 70, the user may again depress the actuator button 28. Once again, the edges 30a, 30b of the gripper 30 are shifted from the retracted position of FIG. 10 toward the extended position of FIG. 11, until the edges 30a, 30b are brought into contact with the needle cover 122. The needle cover 122 is then removed by withdrawing the syringe 106 from the aperture 26. The needle cover 122 is then free to fall into the reservoir 32 should the optional reservoir 32 be attached to the tool 10. The needle 120 is held on the syringe 106 by virtue of the threads 112. It will be appreciated that the aperture 58 in the housing 12 and the area disposed beneath the underside of the actuator button 28 are sized so as to permit placement of the forward portion of the syringe 106 into the tool 10 with either the needle cover in place or the tip cap in place.

In accordance with the disclosed example, the tool 10 may prove especially useful when used in conjunction with, for example, the dosing components shown in FIG. 26. The tool 10 quickly and easily removes the plastic vial cap 128 from the vial 126, the gray tip cap 114 from the prefilled diluent syringe 106, and also removes the plastic needle cover from the needle, which may be any suitable gauge. The container or reservoir 32 is sized to hold a number of the caps from the vial, a number of tip caps from syringe, and a number of needle covers, until the user is ready to dispose of these items.

The following exemplary steps may be followed. In order to remove the plastic vial cap from the vial 126 (the cap of the vial 126 may be color coded), the aperture 20 is located on the housing 12, and the cap is placed in the aperture as shown in, for example, FIG. 26 and as is discussed above. With the vial 126 held sideways with the plastic vial cap against the slot, the vial cap 128 will slide into the slot 22, generally from above. By pressing down on the back or lower end of the vial 126, the plastic vial cap 128 will snap off. The plastic vial cap 128 then drop into the reservoir 32 of the tool 10.

Next, the tip cap is removed from the prefilled diluent syringe as follows. Upon locating the aperture 26 in the housing 12, the user pushes the gray tip cap of the diluent syringe completely into the aperture 26. The user presses down on the actuator button 28 while pulling back on the syringe (i.e.,
while pulling the syringe back out of the aperture 26). This pulls off the tip cap, and the tip cap drops into the reservoir of the tool.

After preparing the dose of medication as described above, the user must remove the plastic needle cover. Again, with the needle and needle cover attached to the syringe, forward end of the syringe is pushed into the aperture 26. The user again presses down on the actuator button on the top of the tool while pulling back on the syringe (again pulling the syringe back out of the aperture). The plastic needle cover will be pulled off and will drop into the reservoir of the tool 10.

The reservoir may be emptied by twisting the housing off the reservoir in a counter-clockwise direction when the tool is viewed from above. The items in the reservoir may then be suitably disposed of.

For travel, the middle part or reservoir can be removed. The smaller tool then can be easily carried in a purse or travel bag. Preferably, the tool is constructed so as to be dishwasher-safe, although many may find it desirable to wash only on the top rack of the dishwasher so as to avoid close contact with a heat source.

Numerous additional modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A tool for use with at least one of a medication vial and a syringe, each of the vial and the syringe having a removable cap, the tool comprising:
    a housing having a top side, a bottom side, and a surrounding edge;
    a first aperture defined in an outer surface of the housing, the first aperture including a flange shaped to engage the vial cap;
    a second aperture defined in the outer surface of the housing, the aperture sized to permit placement of a forward portion of the syringe including the syringe cap into the second aperture;
    an actuator button shiftably mounted to the housing and moveable between a first position and a second position; and
    a gripper mounted within the housing and having a pair of arms, each of the arms biased to a retracted position, the gripper responsive to movement of the actuator button to permit movement of the arms between the retracted position in which the arms are disposed away from a central axis of the second aperture, and an extended position in which the arms are disposed toward the central axis of the second aperture.

2. The tool of claim 1, wherein the gripper comprises biasing means for biasing the actuator button toward the first position.

3. The tool of claim 1, including a spring element engaging the actuator button and arranged to bias the actuator button toward the first position.

4. The tool of claim 1, wherein each arm carries an edge, the edge arranged to engage a portion of the syringe when the syringe is inserted into the second aperture, and the arms are arranged to bias the actuator button toward the first position.

5. The tool of claim 4, wherein the actuator button includes a camming surface, and wherein a portion of the arm is positioned to cam against the camming surface.

6. The tool of claim 1, wherein the arms are responsive to movement of the actuator button to permit simultaneous movement of the arms between the retracted position and the extended position.

7. The tool of claim 6, wherein the arms are attached to a central portion, and the arms are adapted to bias the actuator button toward the first position.

8. The tool of claim 7, wherein each of the arms includes a panel defining an edge, and the panel is arranged to extend perpendicular relative to an axis of the second aperture.

9. The tool of claim 1, wherein the housing includes at least one mounting groove, the mounting groove sized to receive the gripper to thereby permit securement of the gripper within the housing.

10. The tool of claim 1, including a slot defined in the housing adjacent the first aperture, the slot sized to permit passage of the vial cap through the slot.

11. A tool for use with at least one of a medication vial and a syringe, each of the vial and the syringe having a removable cap, the tool comprising:
a housing having a top side, a bottom side, and a surrounding edge;
a first aperture defined in an outer surface of the housing, the first aperture including a flange shaped to engage the vial cap;
a slot defined in the housing adjacent the first aperture, the slot sized to permit passage of the vial cap through the slot;
a second aperture defined in the outer surface of the housing, the aperture sized to permit placement of a forward portion of the syringe including the syringe cap into the second aperture;
an actuator button shiftably mounted to the housing and moveable between a first position and a second position; and
a gripper mounted within the housing and having at least one edge, the gripper responsive to movement of the actuator button to permit movement of the edge between a retracted position in which the edge is disposed away from a central axis of the second aperture, and an extended position in which the edge is disposed toward the central axis of the second aperture,
wherein the housing is attached to a reservoir, the slot in communication with the reservoir, the reservoir being sized to receive a plurality of the vial caps, a lower portion of the housing including a plurality of tabs, an upper portion of the reservoir including a plurality of grooves, the grooves of the reservoir and the tabs of the housing cooperating to permit twisting attachment of the housing to the reservoir.

12. The tool of claim 11, including a base, each of the reservoir and the base including an upper portion having a plurality of grooves, and wherein the housing includes a plurality of tabs sized to engage the grooves of either the reservoir or the base, thereby permitting attachment of the housing to a selected one of the reservoir and the base.

13. The tool of claim 12, wherein a lower portion of the reservoir includes a plurality of tabs sized to engage the grooves of the base thereby permitting attachment of the reservoir to the base.

14. The tool of claim 1, the syringe having a cylindrical barrel, and wherein the second aperture comprises a cylinder sized to receive the barrel.

15. The tool of claim 14, wherein including a flange disposed adjacent an inner and of the cylinder, the flange sized to contact a foreword portion of the syringe to thereby limit travel of the barrel into the cylinder.

16. The tool of claim 1, wherein the actuator button is pivotally mounted to the housing.

17. A tool for use with a medication vial and a syringe, each of the vial and the syringe having a removable cap, the tool comprising:
a housing having a top side, a bottom side, and a surrounding edge;
a slotted aperture defined in an outer surface of the housing, the slotted aperture including a flange shaped to engage the vial cap;
a cylindrical aperture defined in the outer surface of the housing, the cylindrical aperture sized to permit placement of a forward portion of the syringe including the syringe cap into the cylindrical aperture;
an actuator button mounted to the housing; and
a gripper mounted within the housing and having a pair of anns, the gripper responsive to movement of the actuator button to permit movement of the arms between a retracted position in which the arms are disposed away from a central portion of the cylindrical aperture, and an extended position in which the anns are displaced toward the central portion of the cylindrical aperture,
wherein each of the arms is biased towards the retracted position.

18. The tool of claim 17, including a curved seat disposed adjacent the slotted aperture, the seat sized to receive a neck portion of the vial.

19. The tool of claim 18, wherein the slotted aperture is sized to permit passage of the vial cap through the slot.

20. The tool of claim 17, wherein the pair of arms is connected to a central portion of the gripper, and an edge is defined on each of the arms.

21. The tool of claim 17, wherein each of the arms includes a camming surface, each camming surface positioned to contact a portion of the actuator button to thereby bias the actuator button toward a first position corresponding to the retracted position of the gripper.

22. The tool of claim 21, wherein the portion of the actuator button comprises a pair of opposed angled surfaces defined on an underside of the actuator button.

23. The tool of claim 21, wherein each of the arms includes a panel defining an edge, and each panel is arranged to extend perpendicular relative to an axis of the cylindrical aperture.

24. The tool of claim 17, wherein a portion of each of the arms is arranged to cam against the actuator button to thereby bias the actuator button toward a first position corresponding to the retracted position of the gripper.

25. The tool of claim 24, wherein each of the arms is connected to a central portion of the gripper.

26. The tool of claim 17, wherein the housing includes a groove sized to receive the gripper to thereby permit securement of the gripper within the housing.

27. The tool of claim 17, wherein the cylindrical aperture includes a flange disposed adjacent an inner and of the cylindrical aperture, the flange sized to contact a forward portion of the syringe to thereby limit travel of the syringe into the cylindrical aperture.

28. The tool of claim 17, wherein the actuator button is shiftably mounted to the housing and moveable between a first the position corresponding to the retracted position and a second position corresponding to the extended position.

29. The tool of claim 17, wherein the syringe includes at least one of a tip cap and a needle cover, and wherein the arms are adapted to engage either one of the tip cap and the needle cover.

30. A tool for use with a medication vial and a syringe, each of the vial and the syringe having a removable cap, the tool comprising:
a housing having a top side, a bottom side, and a surrounding edge;
a slotted aperture defined in an outer surface of the housing, the slotted aperture including a flange shaped to engage the vial cap;
a cylindrical aperture defined in the outer surface of the housing, the cylindrical aperture sized to permit placement of a forward portion of the syringe including the syringe cap into the cylindrical aperture;
an actuator button mounted to the housing; and
a gripper mounted within the housing and having a pair of opposed edges, the gripper responsive to movement of the actuator button to permit movement of the edges between a retracted position in which the edges are disposed away from a central portion of the cylindrical aperture, and an extended position in which the edges are displaced toward the central portion of the cylindrical aperture,
wherein the housing is attached to a reservoir, the slotted aperture is in communication with the reservoir, and the reservoir is sized to receive a plurality of the vial caps, and wherein a lower portion of the housing includes a plurality of tabs, an upper portion of the reservoir includes a plurality of grooves, the grooves of the reservoir and the tabs of the housing cooperating to permit attachment of the housing to the reservoir.

31. The tool of claim 30, including a base, each of the reservoir and the base including an upper portion having a plurality of grooves, and wherein the housing includes a lower portion having a plurality of tabs sized to engage the grooves of either the reservoir or the base, thereby permitting attachment of the housing to a selected one of the reservoir and the base.

32. The tool of claim 31, wherein a lower portion of the reservoir includes a plurality of tabs sized to engage the grooves of the base thereby permitting attachment of the reservoir to the base.

33. A tool system comprising:
a syringe having a generally cylindrical forward portion and at least one of a tip cap and a needle cover;
a medication vial having a neck and a removable cap;
a tool, the tool comprising:
a housing having a slotted aperture in an outer surface of the housing, the slotted aperture including a flange shaped to engage the vial cap, the housing further including a cylindrical aperture in the outer surface of the housing, the cylindrical aperture sized to permit placement of the forward portion of the syringe including at least one of the syringe cap and the needle cover into the cylindrical aperture;
an actuator button mounted to the housing; and
a gripper including a pair of arms disposed within the housing, the arms responsive to movement of the actuator button between a first position and a second position, the arms when in the first position are disposed away from a central portion of the cylindrical aperture, the arms, when in the second position, are disposed toward the central portion of the cylindrical aperture,
wherein the arms are biased away from one another towards the first position.

34. The tool system of claim 33, wherein the tool includes a curved seat disposed adjacent the slotted aperture, the seat sized to receive the neck portion of the vial, the flange sized to grip and remove the vial cap in response to movement of the vial relative to the housing.

35. The tool system of claim 33, wherein the slotted aperture of the tool is sized to permit passage of the vial cap through the slot, and including a reservoir sized to receive the removed vial cap.

36. The tool system of claim 33, wherein the arms of the tool are attached to a central portion of the gripper.

37. The tool system of claim 36, wherein each of the arms of the tool comprises an edge defined on a corresponding one of the arms, each edge arranged to extend perpendicular relative to an axis of the cylindrical aperture.

38. The tool system of claim 33, wherein each of the arms of the tool includes a camming surface, each camming surface positioned to contact a portion of the actuator button to thereby bias the actuator button toward a first position corresponding to the retracted position of the arms.

39. The tool system of claim 38, wherein the portion of the actuator button of the tool comprises a pair of angled surfaces defined on an underside of the actuator button.

40. The tool system of claim 33, wherein the housing of the tool includes a seat sized to receive the gripper to thereby permit securement of the gripper within the housing.

41. The tool system of claim 33, wherein the cylindrical aperture of the tool includes a stop flange disposed adjacent an inner and of the cylindrical aperture, the stop flange sized to contact the forward portion of the syringe to thereby limit travel of the syringe into the cylindrical aperture.

42. The tool system of claim 33, wherein the actuator button of the tool is pivotally mounted to the housing and moveable between a first the position corresponding to the retracted position of the gripper and a second position corresponding to the extended position of the gripper.

43. A tool system comprising:
a syringe having a generally cylindrical forward portion and at least one of a tip cap and a needle cover;
a medication vial having a neck and a removable cap;
a tool, the tool comprising:
a housing having a slotted aperture in an outer surface of the housing, the slotted aperture including a flange shaped to engage the vial cap, the housing further including a cylindrical aperture in the outer surface of the housing, the cylindrical aperture sized to permit placement of the forward portion of the syringe including at least one of the syringe cap and the needle cover into the cylindrical aperture;
an actuator button mounted to the housing; and
a pair of grippers disposed within the housing, the grippers responsive to movement of the actuator button between a first position and a second position, the grippers when in the first position are disposed away from a central portion of the cylindrical aperture, the gripers when in the second position are disposed toward the central portion of the cylindrical aperture,
wherein the housing is attached to a reservoir, the slotted aperture in communication with the reservoir, the reservoir sized to receive a plurality of the vial caps and a plurality of at least one of the needle cover and the needle cap, the tool including a base, each of the reservoir and the base including an upper portion, and wherein a lower portion of the housing is adapted for releasable attachment to the upper portion of a selected one of the reservoir and the base.

44. The tool system of claim 43, wherein a lower portion of the housing of the tool is attached to an upper portion of the reservoir.

45. The tool system of claim 44, wherein the lower portion of the housing of the tool and the upper portion of the reservoir comprises a tab in groove connection.

46. A method of preparing medication for delivery to a user comprising the steps of:
- providing a syringe having a generally cylindrical forward portion and at least one of a tip cap and a needle cover;
- providing a medication vial having a neck and a removable cap;
- providing a tool adapted to remove a selected one of the tip cap and the needle cover from the syringe and further adapted to remove the cap from the medication vial;
- providing the tool with a slotted aperture having a flange shaped to engage the vial cap;
- providing the tool with a cylindrical aperture sized to permit placement of the forward portion of the syringe including at least one of the syringe cap and the needle cover into the cylindrical aperture;
- providing a gripper having a pair of arms disposed on opposite sides of the cylindrical aperture, the arms responsive to movement of an actuator button, the actuator button permitting generally simultaneous movement of the arms between a retracted position and an extended position, the arms biased towards the retracted position;
- positioning the medication vial in the slotted aperture with the vial cap engaging the flange;
- shifting the medication vial relative to the housing such that the cap is removed from the vial;
- placing the forward portion of the syringe into the cylindrical aperture until the forward portion of the syringe abuts the stop flange;
- moving the actuator button such that the arms grip a removable component on the syringe; and
- withdrawing the syringe from the cylindrical aperture such that the removable component is removed form the syringe.

* * * * *